United States Patent [19]

Voorhees

[11] 4,308,623
[45] Jan. 5, 1982

[54] DISPOSABLE FLUID-TIGHT EAR PROTECTOR

[76] Inventor: Donna S. Voorhees, 3353 Rubio Crest Dr., Altadena, Calif. 91051

[21] Appl. No.: 178,864

[22] Filed: Aug. 18, 1980

[51] Int. Cl.³ .......................................... A41D 21/00
[52] U.S. Cl. ........................................ 2/174; 2/209; 2/243 R; 128/151
[58] Field of Search ................ 2/209, 174, 192, 206, 2/243 R, 243 B; 128/151, 157

[56] References Cited

U.S. PATENT DOCUMENTS

| | | | |
|---|---|---|---|
| 2,198,546 | 4/1940 | Lover et al. | 2/174 |
| 2,378,398 | 6/1945 | Fiedler | 2/209 |
| 2,570,675 | 10/1951 | Morris | 128/151 |
| 3,841,325 | 10/1974 | Pickard | 128/157 X |
| 4,134,153 | 1/1979 | Voorhees | 128/151 X |

Primary Examiner—Peter P. Nerbun
Attorney, Agent, or Firm—Sellers and Brace

[57] ABSTRACT

A protective enclosure for the human ear entirely closed except for a single opening sized to receive the outer ear. This opening is surrounded by a band of pressure sensitive adhesive to anchor the enclosure to the skull in a fluid tight manner. The opposite lateral edges of the enclosure are pleated inwardly to receive the operator's fingers in areas closely spaced to the adhesive while installing the enclosure over the ear.

10 Claims, 3 Drawing Figures

U.S. Patent  Jan. 5, 1982  4,308,623
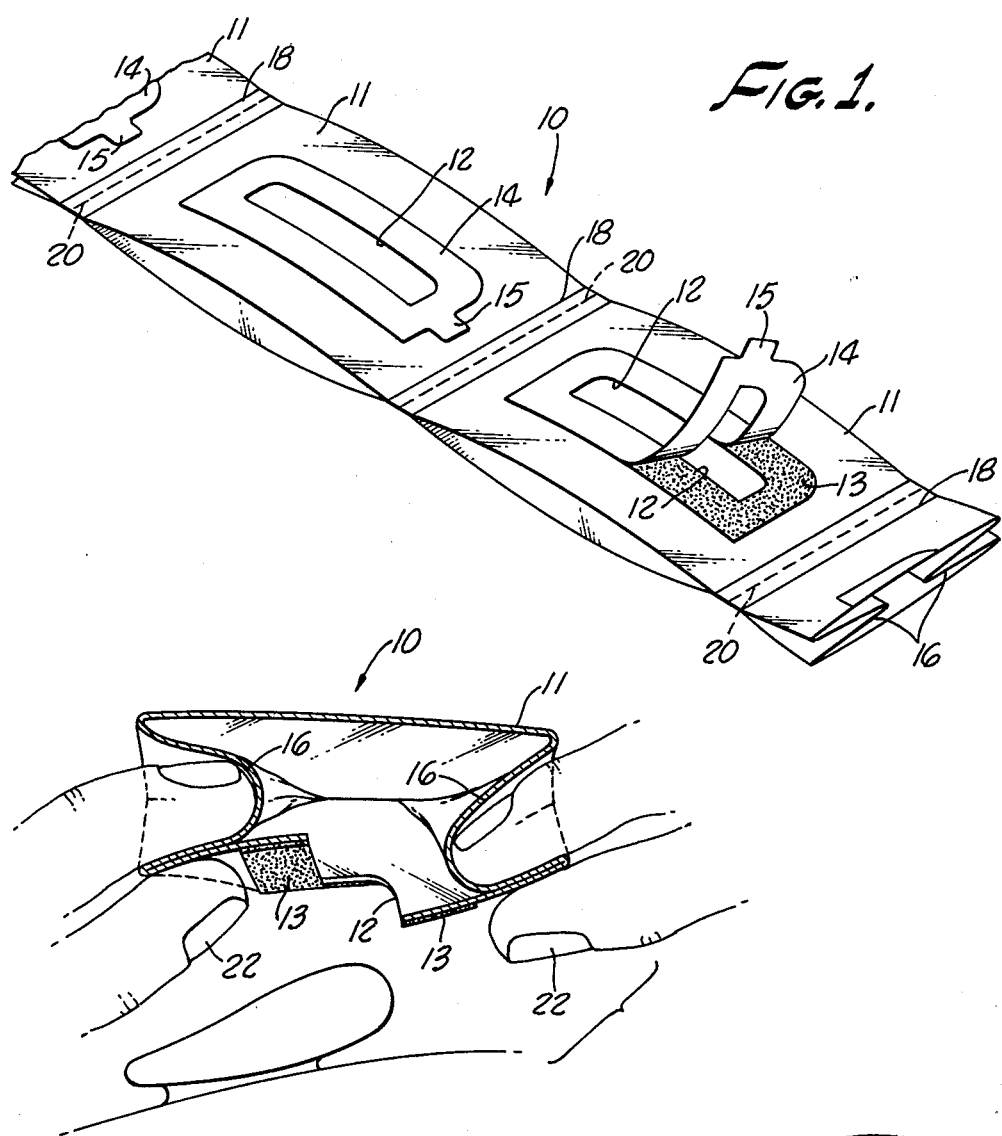
FIG. 1.
FIG. 2.
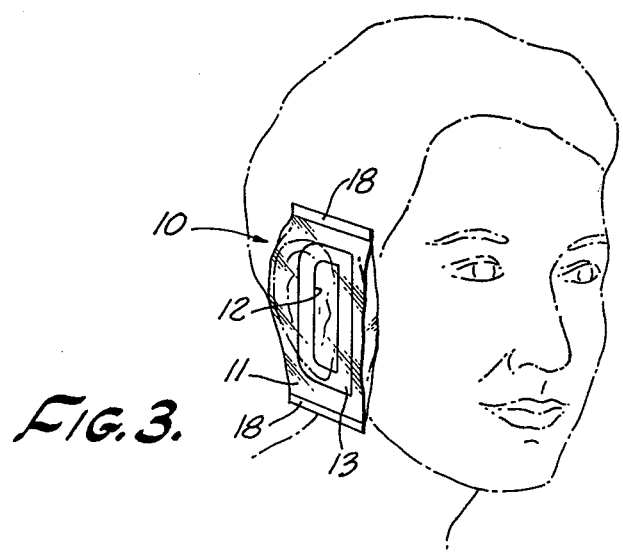
FIG. 3.

DISPOSABLE FLUID-TIGHT EAR PROTECTOR

This invention relates to an ear protector, and more particularly to an inexpensive single use fluid-tight enclosure having a single opening to receive the ear and encircled by a layer of adhesive material adherent to the skull at the base of the ear.

Many persons are afflicted with ear conditions requiring the exercise of extreme caution against the entry of foreign matter of either a fluid or a solid nature. All necessary precautions must be taken to avoid exposure of the ear to a wide range of weather conditions, dust-laden air and moisture or fluids. Other common hazards include those encountered in bathing, taking showers, washing the scalp or having the hair dressed by a beautician unfamiliar with the risk incurred by persons so afflicted.

Various proposals made heretofore to safeguard against the foregoing and other hazards are mentioned in the opening paragraphs of my own prior U.S. Pat. No. 4,134,153, granted Aug. 3rd, 1978. The ear protector construction disclosed in that patent avoids the numerous shortcomings and disadvantages of prior proposals but is not as convenient to apply, nor as reliable and foolproof in excluding foreign matter as my present invention. My prior construction employs a single large plaque of plastic material assembled over the ear by gathering it from its opposite sides. Thereafter all edges are gathered together about the ear and secured by applying a rubber band, a twist wire or the like. If this operation is not performed with due care the gathered material can leak or become loose or untied at an inopportune time and expose the ear to serious hazards.

SUMMARY OF THE INVENTION

The present invention avoids these and other disadvantages and shortcomings, and provides a highly reliable, inxpensive, single use ear protector. The protector comprises an envelope which is fully closed except for a single opening sized to receive the outer ear. Assembly of the envelope about the ear is aided and facilitated by providing its opposite edges with inwardly extending pleats receptive of the user's forefingers and thumbs to grasp the envelope closely adjacent the exposed adhesive material while guiding the ear through the opening. Thereafter the pleats enable the forefingers to press the ringlet of adhesive firmly against the skull leaving the ear fully enclosed in a snug fitting fluid tight enclosure.

Accordingly, it is a primary object of the present invention to provide an improved inexpensive throwaway protector for enclosing the ear to preclude the entry of moisture and foreign matter.

Another object of the invention is the provision of an ear protector comprising a film-like envelope of supple, impervious material having a single opening into its interior through which the ear is inserted and surrounded on its exterior by a band of pressure sensitive adhesive for sealing the opening to the skull at the base of the ear.

These and other more specific objects will appear upon reading the following specification and claims and upon considering in connection therewith the attached drawing to which they relate.

Referring now to the drawing in which a preferred embodiment of the invention is illustrated:

FIG. 1 is a perspective view of an illustrative embodiment of my improved ear protector separably attached to one another prior to use;

FIG. 2 is a cross sectional view through one of the protectors in the process of being assembled over an ear; and FIG. 3 is a perspective view showing one of the protectors assembled to a person's ear.

Referring to FIG. 1, there is shown an illustrative embodiment of the single use waterproof ear protector, designated generally 10, a series of which are separably connected to one another in end-to-end relationship. The protectors are conveniently formed from seamless thermo-plastic tubing such as polyvinyl chloride, polyethelene, or the like, typically having a thickness of two to three mils. Plastic films of a wide variety of composition are suitable in practising this invention because of their supple character and imperviousness to moisture and other foreign material. Another important characteristic is the ease with which the walls of such material can be heat-fused and sealed to one another.

A continuous length of the tubing 11 is provided at intervals with an elongated ear receiving opening 12. The area surrounding the rim of this opening is provided with a layer of pressure sensitive adhesive 13 of a type well known in the adhesive art as non-reactive with or harmful to the skin. A suitable adhesive meeting these requirements is obtainable from The Mercury Label Company and is identified by that supplier by the designators FC-290. This adhesive is firmly adherent to plastic 11 and is preferably protected until application to the skin by a masking cover 14 readily peelable from layer 13 at the time of use. Desirably, this mask includes a thumb-tab 15 extending beyond the edge of coating 13 to facilitate its removal.

Preferably, the opposite lateral sides of each ear protector envelope are provided with an inwardly extending pleat 16. These pleats have a two-fold purpose, namely, permitting the protective enclosure 11 to expand to accommodate the outer ear without pressure by an envelope having an outer perimeter only slightly larger than the length and breadth of the ear and, secondly, greatly facilitating assembly of the envelope over the ear.

After pleats 16 have been formed and envelope 11 has been flattened, its opposite ends are sealed closed, such as by the well known heat-fusion technique. As shown, this seal comprises a heat-fused sealing band 18 extending crosswise of the opposite end of each envelope 11 and is effective to seal the outer surfaces of the pleats to one another and the inner surfaces and to the adjacent inner surfaces of the envelope as well as the portions of the envelope walls between the inner edges of the pleats to one another. In consequence each envelope is fully sealed closed except for the single ear receiving opening 12.

Each of the sealing bands 18 is preferably provided medially of its lateral edges with a row of severance perforations 20 whereby the leading one or more of a series of interconnected envelopes can be readily detached for individual use.

The assembly of the ear protector envelopes 11 to one or both ears of the user is accomplished expeditiously and without need for tools, tie strings or fasteners of any kind. A leading one of the packaged series of envelopes is detached by severance along the perforations 20. Pull tape 15 is then lifted to separate mask 14 from the adhesive layer 13. Thereafter the user inserts either the thumb or forefinger of each hand into pleats 16 between the opposite ends of opening 12 with his one finger 22 pressing against the exterior of the envelope in the area outwardly of adhesive 13. The expanded envelope is then manipulated in the manner clearly illustrated in FIG. 2 to insert the outer ear through opening 12. Once this has been accomplished, the pleats enable the user to press his finger further inwardly and run it along the area overlying the adhesive to ensure that the full length thereof is firmly pressed against and adherent to the skull surrounding the base of the ear. The entire outer ear is now sealed by the impervious envelope and foreign matter of neither a solid nor a liquid nature can enter the ear. The user may proceed to wash and dress the hair, to take showers or even to go swimming without fear or risk of foreign matter entering into the ear.

While the particular disposable fluid-tight ear protector herein shown and disclosed in detail is fully capable of attaining the objects and providing the advantages hereinbefore stated, it is to be understood that it is merely illustrative of the presently preferred embodiment of the invention and that no limitations are intended to the detail of construction or design herein shown other than as defined in the appended claims.

I claim:

1. A fluid tight single use protector for the outer ear comprising:
   a one-piece tubular enclosure of impervious flexible film material sealed closed at both ends and sized for assembly about a person's outer ear and fully closed except for a single opening in one sidewall to receive the outer ear; and
   a layer of pressure sensitive adhesive applied to the exterior of said enclosure surrounding said single opening and effective to hold said enclosure sealed to a person's skull in a fluid-tight manner in an area surrounding the base of the outer ear.

2. An ear protector as defined in claim 1 characterized in that said tubular enclosure is elongated and sealed closed crosswise of the opposite ends thereof.

3. An ear protector as defined in claim 1 characterized in that said tubular enclosure is formed of tubular thermoplastic film material heat-sealed closed across the opposite ends thereof.

4. An ear protector as defined in claim 1 characterized in that said tubular enclosure has a pleat extending along at least one side of aid single opening into which a person can insert a finger to grip said enclosure between his finger and thumb while inserting the outer ear through said single opening.

5. An ear protector as defined in claim 4 characterized in that said tubular enclosure has a pleat extending along the opposite sides of said single opening.

6. An ear protector as defined in claim 4 characterized in that said protector is separably attached to a series of said tubular enclosures in end-to-end relationship and separable from one another prior to use along a row of perforations extending crosswise of the opposite ends of said enclosures between the remote lateral edges of the adjacent sealed ends of contiguous ones of said protectors.

7. A series of individual single use ear protectors separably interconnected in end-to-end relation comprising: a continuous length of flattened tubing of impervious film material having a pleat along at least one lateral side thereof and located between the flattened walls of said tubing, the opposite ends of said tubing including the walls of said pleat being sealed to one another in a fluid tight manner by a sealing band extending crosswise of said tubing at spaced apart intervals to divide said tubing into a series of expandable compartments; an outer ear receiving opening through one sidewall of each of said compartments surrounded about the rim thereof with a band of pressure sensitive adhesive for holding said expandable compartment sealed to a person's skull in a ring embracing the base of his ear; a row of severance perforations crosswise of said tubing between the lateral edges of said sealing band to facilitate the detachment of said protectors from one another; and a readily detachable mask applied over each of said bands of adhesive.

8. A series of interconnected ear protectors as defined in claim 7 characterized in that said tubing is formed of thermoplastic tubing, and said sealing bands comprise heat fused portions of said tubing.

9. A fluid-tight single use protector for the outer ear comprising: a tubular enclosure of flexible thermoplastic film sealed closed at both ends and having a single opening into the interior thereof midway between said sealed ends, said opening being sized to receive the outer ear and being coated about the exterior rim portion thereof with pressure sensitive adhesive effective to hold said tubular enclosure sealed to the skull about the base of an ear in a fluid-tight manner.

10. An ear protector as defined in claim 9 characterized in that said single opening is elongated and located between a pair of inwardly extending pleats formed from the thermoplastic film of said tubular enclosure.

* * * * *